(12) United States Patent
Woodroof et al.

(10) Patent No.: US 10,182,900 B2
(45) Date of Patent: *Jan. 22, 2019

(54) HERNIA REPAIR DEVICE AND METHOD

(71) Applicants: E. Aubrey Woodroof, Carlsbad, CA (US); Lipton Laverne Martin, Fork, SC (US)

(72) Inventors: E. Aubrey Woodroof, Carlsbad, CA (US); Lipton Laverne Martin, Fork, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/469,891

(22) Filed: Mar. 27, 2017

(65) Prior Publication Data
US 2018/0250114 A1    Sep. 6, 2018

Related U.S. Application Data

(63) Continuation-in-part of application No. 15/451,078, filed on Mar. 6, 2017.

(51) Int. Cl.
*A61F 2/00* (2006.01)
*A61L 31/02* (2006.01)
*A61L 31/04* (2006.01)
*A61L 31/16* (2006.01)
*A61L 31/14* (2006.01)
*A61L 31/06* (2006.01)

(52) U.S. Cl.
CPC .......... *A61F 2/0063* (2013.01); *A61F 2/0077* (2013.01); *A61L 31/028* (2013.01); *A61L 31/048* (2013.01); *A61L 31/06* (2013.01); *A61L 31/146* (2013.01); *A61L 31/16* (2013.01); *A61F 2002/009* (2013.01); *A61F 2002/0068* (2013.01); *A61F 2250/0067* (2013.01)

(58) Field of Classification Search
CPC ...................................... A61F 13/00
USPC ... 623/1.41, 15.11–15.12, 23.72–23.76, 926; 424/443, 447; 435/396–408; 602/42–47
See application file for complete search history.

(56) References Cited

U.S. PATENT DOCUMENTS 7,815,931 B2 * 10/2010 Woodroof ............... A61L 27/60
424/443

* cited by examiner

*Primary Examiner* — Yashita Sharma
(74) *Attorney, Agent, or Firm* — Stevem W. Webb

(57) ABSTRACT

An improved abdominal hernia repair system is presented comprised of a silicone layer backed up with a knitted or woven polypropylene fabric layer, the silicone layer possessing a regular pattern of slits that permit equilibration of fluid pressure across the device. A variety of therapeutic substances can be applied to the hernia repair device to promote healing, including aloe and other medicinal preparations.

An improved inguinal hernia repair system is presented that is identical to the above except it does not contain the hydrophobic silicone component.

4 Claims, 2 Drawing Sheets

HERNIA REPAIR DEVICE AND METHOD

RELATED APPLICATIONS

This application is a Continuation-In-Part of U.S. patent application Ser. No. 15/451,078 filed 6 Mar. 2017, which is currently co-pending.

FIELD OF INVENTION

The present invention relates to surgically-implantable prostheses that limit the incidence of postoperative adhesions utilizing a smooth 2D hydrophobic silicone surface. Secondly, this invention seeks to improve the biocompatibility of synthetic 3D mesh structures so that autogenous tissue will more readily grow into same during the healing process. This is accomplished by coating the 3D mesh surface with hydrophillic and hygroscopic biocompatible materials. Specifically, this invention relates to the field of hernia repair prostheses.

BACKGROUND OF THE INVENTION

Prosthetic mesh materials and the like have been used to reinforce the abdominal wall and to close abdominal wall defects. Polypropylene (PP) mesh is one of the most widely used and successful hernia mesh device. Polyester (POL) and porous teflon (PTFE) are also currently used. In many cases, including incisional and umbilical hernia repair and chest reconstruction, prosthetic mesh structures will come into direct contact with the abdominal viscera. Postoperative adhesions between the mesh and the intestine may occur, potentially leading to intestinal fistulization, and other problems.

The prior art contains several attempts to minimize postoperative adhesions associated with prosthetic mesh materials. Covering the prosthesis with peritoneum or other tissue to form a biological barrier between the implant and the bowel is one approach. Placement of a physical barrier between the surgical site and the surrounding tissue where adhesions are most commonly encountered is another.

The Ventrio Hernia Patch (BARD Davol, Inc. Warwick, R.I.) is a multi-layer hernia repair device with a PTFE surface adjacent to the visceral abdominal cavity. PTFE is hydrophobic and resists adhesions.

U.S. Pat. No. 5,002,551 discloses a physical barrier formed of a knitted oxidized regenerated cellulose (Intercede(TC7)). The patent teaches that other physical barriers can include silicone elastomers and absorbable gelatin films. Based on studies in the literature, such physical barriers alone are not sufficient to reinforce the abdominal wall or to repair abdominal wall defects.

Jenkins et al., "A Comparison of Prosthetic Materials Used to Repair Abdominal Wall Defects", Surgery, Vol. 94, No. 2, August 1983, pg. 392-398, describes a technique of placing an absorbable gelatin film (Gelfilm®) freely between a piece of Marlex® knitted polypropylene monofilament mesh and the abdominal viscera. The gelatin film dissolved after one week. Thereafter, the incidence of adhesions was reported to be the same as with using the Marlex mesh alone.

Several existing products address this problem:

Cousin Biotech Intramesh® T1, a two-sided polypropylene and ePTFE wall reconstruction prosthesis. Its two-sided structure has the advantage of one smooth side which reduces visceral adherence and a knitted side for better colonization of the peritoneum. One side in polypropylene monofilament knit, the other smooth anti-adhesive ePTFE.

Ethicon (Johnson&Johnson)—ULTRAPRO Partially Absorbable Lightweight Mesh. This was the first partially absorbable mesh available in the United States. They claim strong, secure repair with a flexible scar that lets abdominal wall move more naturally, as well as construction with trusted, proven materials.

Therapeutic options to treat excessive scarring are limited and most are not proven to be effective. Gram-negative or gram-positive antimicrobials (vancomycin, ramplianin, linezolid, could be added to the biological coating of the 3D matrix or incorporated into the solid silicone membrane if desired.

SUMMARY OF THE INVENTION

The present invention is a device or prosthesis for reinforcing and repairing a weakened muscular that limits the incidence of postoperative adhesions, as well as providing a means for introducing therapeutic materials to the wound site. The device or prosthesis is formed of a biologically compatible, flexible and non-porous implantable material that reinforces tissue and closes tissue defects, particularly in the abdominal cavity, and a non-porous barrier that physically isolates the reinforcing material from areas likely to form adhesions, such as the abdominal viscera. The barrier and implantable material are permanently attached by a manner which provides a wealth of openings in the material for tissue ingrowth.

In one aspect, the present invention provides a device containing two layers of material, the first layer of material, an upper layer, comprised of a silicone membrane, the second layer, a lower layer, comprised of a woven polypropylene fiber fabric, the silicone membrane selected in a thickness from 0.001" to 0.005", the upper layer possessing a plurality of slits in its surface, said slits made after the two layers are joined together, said slits in a regular pattern, the regular pattern comprising alternating perpendicular orientation, both horizontal and vertical, the lower layer woven in a regular pattern with weft knitting using a 1×1 alternating stitch, the slits on the surface either following the weft direction of the lower layer or crossing the weft direction of the lower layer perpendicularly, said upper layer or said lower layer or both the upper and lower layers treated with a plurality of layers of medicinal or therapeutic substances, said lower layer and optionally said upper layer also treated with a water soluble or water insoluble anti-scar compound, said slits placed in said upper layer such that the hernia repair device has essentially zero porosity with no stretching tension placed on it, the porosity of said hernia repair device variable proportional to the amount of stretching tension and the direction in which said stretching tension is placed on the hernia repair device, the direction of stretching tension dependent on the orientation of said slits with the weft orientation of a woven fiber fabric, the hernia repair device designed to place the woven nylon fabric side towards the abdominal wall when in use.

For repair of abdominal hernia's, it is minimally desired that there be one surface facing the gut that is non-adhesive and a surface facing away from the gut that permits tissue ingrowth, can become vascularized, and is indefinitely stable.

In the preferred embodiment of the invention, the invention is comprised of attached sheets of knitted Polypropylene monofilament mesh fabric and a silicone elastomer. The mesh will be created using weft knitting using a 1×1 alternating stitch. The silicone is a non-porous membrane approximately 0.001" thick. An optional seam is stitched around the edge of the membrane to provide strength and control elongation of the invention as applied to a rupture.

An alternate embodiment of the invention is to have an extra bead of RTV silicone applied around the edge of the device or prosthesis, which would be molded in during the layering process. Because of its composition, the invention is light, translucent, and very flexible.

Addition of hypoallergenic Type I porcine collagen peptide or other biologicals (e.g. Immuno-10®), is possible for therapeutic purposes. These materials would be added to the mesh side of the invention.

The synthetic components of the invention except for the gelatin are stable in vivo and resistant to mammalian enzymes.

It is an object of the invention to provide a large pore mesh to produce "tension-free" repair, without too much stretch or elongation (not greater than 35%) but still thin and can be inserted with a large bore needle using laparoscopic technique.

It is an object of the invention to provide a prosthesis which combines the attributes of a light-weight porous surgical mesh fabric and a hydrophobic physical barrier.

It is an object of the invention to add cured "Unrestricted" medical grade silicone membrane (0.001" to 0.002" thick) physically bonded to one side of the 3 dimensional polypropylene mesh to provide a 2 dimensional hydrophobic smooth silicone surface towards the gut that resists adhesions.

It is an object of the invention to coat the 3D polypropylene surface with a proprietary mixture of gelatin/Aloe to create a hydrophillic/hygroscopic surface that autogenous muscle and connective tissue will readily grow into.

It is a further object of the invention to provide a device or a prosthesis which stimulates tissue infiltration into the light-weight porous 3 dimensional polypropylene mesh without inflammation of the abdominal viscera.

It is a further object of the invention that the prosthesis can be sterilized with E-beam irradiation and will have an expected three-year shelf life at room temperature.

It is a further object of the invention that it be thin, strong (hold sutures, staples and the like), transparent, very flexible; stretchable, conformable, stable indefinitely in biological systems (in vivo humans), and biocompatible: sterile, non-toxic, hypoallergenic, and non-pyrogenic.

It is a further object of the invention that the silicon, smooth surface of the device possesses slits of a characteristic length in an alternating pattern, said slits when closed possessing essentially zero porosity.

DETAILED DESCRIPTION OF THE INVENTION

The invention (when used as for repair of abdominal hernia repair) is directed to a device comprised of two layers or sheets of material, the first layer of material, an upper layer, comprised of a silicone membrane or sheet and the second layer, a lower layer, comprised of a knitted or woven polypropylene fiber fabric.

In one embodiment, the silicone membrane or sheet is a smooth membrane or sheet. The silicone layer/sheet and the woven fiber fabric are brought together at time of manufacture by implanting the woven fiber fabric into the silicone membrane or sheet while said silicone membrane or sheet is still soft. A portion of the woven fiber fabric implants itself in the material of the silicone membrane or sheet leaving a thickness of the woven material above the level of the silicone membrane or sheet. The resultant material is a 3 dimensional mesh.

In another embodiment, the 3 dimensional mesh is a polypropylene mesh. In one embodiment, the mesh is coated with a mixture of gelatin/Immuno-10® to enhance ingrowth/healing. The invention for non-abdominal hernia repair (inguinal, other) will not have the silicone component but will have the 3 dimensional polypropylene mesh coated with a mixture of gelatin/Immuno-10® to enhance ingrowth/healing.

Figure 1:
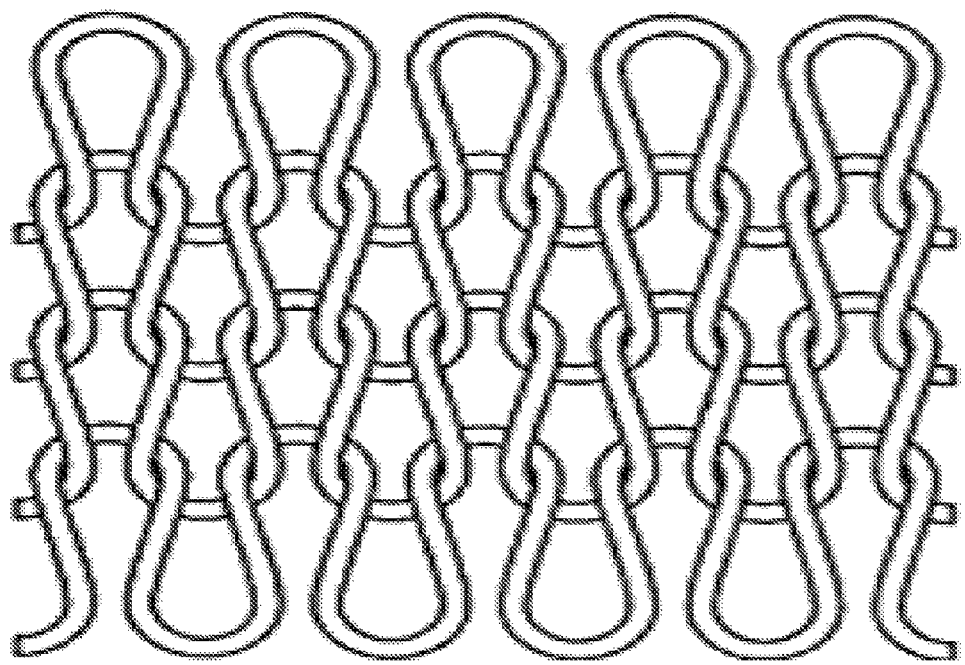
FIG. 1. Weft knitting pattern as used in the device
FIG. 2. Slit pattern on the smooth side of the device

In one embodiment, the woven fiber fabric is comprised of knitted polypropylene monofilament mesh fabric, the mesh is created using weft knitting using a 1×1 alternating stitch, the detailed knit pattern shown in FIG. 1.

The woven material above the silicone membrane or sheet, the "woven side" of the invention, can be impregnated or incorporated with biological and non-biological substances for therapeutic purposes. These substances include but are not limited to hypoallergenic Type I porcine collagen peptide, Immuno-10®, and extracellular matrix, or a combination of any of the substances thereof.

The amounts of biological and non-biological substances for therapeutic purposes are as follows for the preferred embodiment: the amount of gelatin is about 20 micrograms/square cm ($cm^2$); about 40 micrograms of Immuno-10®/square cm.

Figure 2:
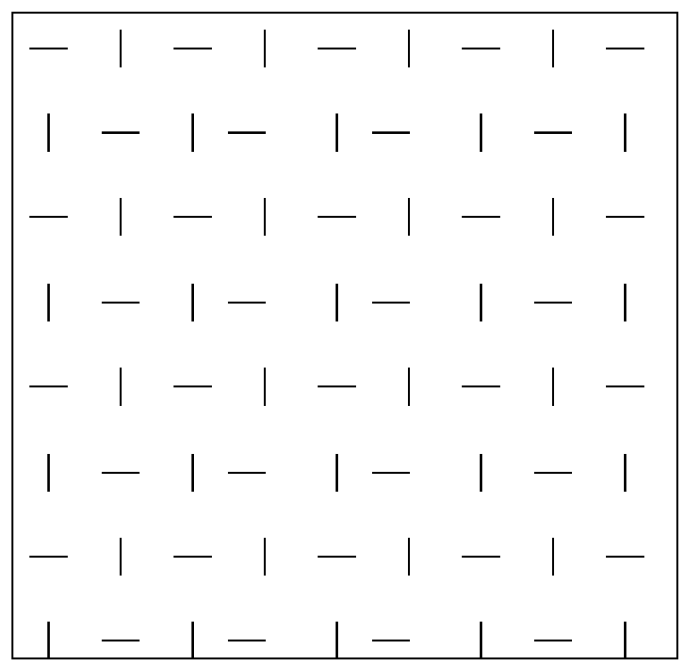

As in FIG. 2, openings are made after the silicone component has been cured, and are in the shape of slits, not holes. The figure shows the hernia repair device silicone layer up with the slits exposed.

The present invention differs from its ancestors in that it has "variable porosity"; the slit size in the thin silicone will be essentially zero (with no stretch, in relaxed mode) with essentially zero porosity to a higher porosity (proportional to the stretch applied). The stretching will come from buildups of fluid between the smooth side of the invention and the abdominal wall, which would be relieved as the slits are opened by pressure on the membrane. Slightly open slits allow fluid to cross the device and not accumulate (as a seroma) which could become infected.

In this embodiment, designed for hernia repair, the slits made in the silicone are approximately 0.044" long with a space of 0.180" between the centers of the slits; rows of slits are 0.250" apart. The rows of slits are arranged such that the slits alternate orientations, half are parallel to the "weft" orientation of the knitted polypropylene component, the other half perpendicular to it.

In the preferred embodiment, there is an additional bead of silicone that is added to the "smooth side" of the invention, on the surface of the silicone sheet, around the edge of the invention. This bead of silicone assists the surgeon implanting the device by giving the surgeon something to grip with forceps. Without the bead of silicone, the edge of the invention could slip out of a forceps during implantation.

This is the preferred embodiment of the invention. The technology to create this invention is listed as the preferred embodiment of this invention, but other methods are possible and are within the contemplation of this patent.

What is claimed is:

1. A hernia repair device, the hernia repair device comprised of two layers of material,
   the first layer of material, an upper layer, comprised of a silicone membrane, the second layer, a lower layer, comprised of a woven polypropylene fiber fabric,
   the silicone membrane selected in a thickness from 0.001" to 0.005",
   the upper layer possessing a plurality of slits in its surface, said slits made after the two layers are joined together, said slits in a regular pattern, the regular pattern comprising alternating perpendicular orientation, both horizontal and vertical,
   the lower layer woven in a regular pattern with weft knitting using a 1×1 alternating stitch, the slits on the surface either following the weft direction of the lower layer or crossing the weft direction of the lower layer perpendicularly,
   said upper layer or said lower layer or both the upper and lower layers treated with a plurality of layers of medicinal or therapeutic substances,
   said slits placed in said upper layer such that the hernia repair device has essentially zero porosity with no stretching tension placed on it,
   the porosity of said hernia repair device variable proportional to the amount of stretching tension and the direction in which said stretching tension is placed on the hernia repair device,
   the direction of stretching tension dependent on the orientation of said slits with the weft orientation of a woven fiber fabric,
   the hernia repair device designed to place the woven nylon fabric side towards the abdominal wall when in use.

2. The hernia repair device of claim 1 where the plurality of layers of medicinal and therapeutic substances are selected from the list of hypoallergenic Type I porcine collagen peptide , pure aloe, aloesin, and extracellular matrix.

3. The device of claim 1, wherein the upper layer is comprised of a smooth silicone membrane.

4. The device of claim 1, wherein the device is for hernia repair.

* * * * *